United States Patent [19]

Allington et al.

[11] Patent Number: 4,863,592
[45] Date of Patent: Sep. 5, 1989

[54] APPARATUS FOR REDUCING TAILING IN A LIQUID CHROMATOGRAPH

[75] Inventors: Robert W. Allington; Abolghassem Y. Tehrani; John N. Jones, all of Lincoln, Nebr.

[73] Assignee: Isco, Inc., Lincoln, Nebr.

[21] Appl. No.: 117,371

[22] Filed: Oct. 28, 1987

Related U.S. Application Data

[63] Continuation of Ser. No. 745,512, Jun. 17, 1985, abandoned, which is a continuation-in-part of Ser. No. 585,298, Mar. 1, 1984, Pat. No. 4,545,904.

[51] Int. Cl.$^4$ .............................................. B01D 15/08
[52] U.S. Cl. ................. 210/96.1; 210/198.2; 210/510.1; 422/70
[58] Field of Search .......... 210/198.2, 510.1, 656–659, 210/96.1; 55/67, 386; 422/70

[56] References Cited

U.S. PATENT DOCUMENTS

| | | | |
|---|---|---|---|
| 2,604,958 | 7/1952 | Leufvenius | 210/510.1 |
| 3,250,395 | 5/1966 | Blume | 210/198.2 |
| 3,440,864 | 4/1969 | Blume | 210/198.2 |
| 3,855,130 | 12/1974 | Randau | 210/198.2 |
| 3,978,575 | 9/1976 | Beyer | 210/198.2 |
| 4,399,032 | 8/1983 | Mott | 210/198.2 |
| 4,451,365 | 5/1984 | Sattler | 210/198.2 |
| 4,462,962 | 7/1984 | Baba | 422/70 |
| 4,469,597 | 9/1984 | Mott | 210/198.2 |
| 4,545,904 | 10/1985 | Tehrani | 210/198.2 |

*Primary Examiner*—Ernest G. Therkorn
*Attorney, Agent, or Firm*—Vincent L. Carney

[57] ABSTRACT

To reduce tailing, the frit at the outlet to the liquid chromatographic column has a diameter substantially equal to that of the inside diameter of the outlet end of the column and less than two millimeters. It is held directly against the packing of the column within a cylindrical member having a shoulder with a central aperture at least the size of the diameter of the frit and cylindrical walls which are fastened to resist force in the direction of the axis of the column from its inlet to its outlet. A gasket seals the cylindrical holder against the column wall. The frit is formed of gold-plated nickel spheres sintered together at a temperature lower than the gold-nickel eutectic temperature of 950 degrees Celsius but above the phase-immiscibility temperature of 720 degrees Celsius. The size and shape of the frit is selected to reduce tailing by causing the flow path from the column to be uniform.

15 Claims, 5 Drawing Sheets

APPARATUS FOR REDUCING TAILING IN A LIQUID CHROMATOGRAPH

REFERENCE TO RELATED APPLICATIONS

This application is a continuation of application Ser. No. 745,512, filed June 17, 1985, now abandoned, which is a continuation-in-part of U.S. application 585,298 for Apparatus for Reducing Tailing in a Liquid Chromatograph filed by Robert W. Allington et al on Mar. 1, 1984, now U.S. Pat. No. 4,545,904, and assigned to the same assignee as this application.

BACKGROUND OF THE INVENTION

This invention relates to liquid chromatographic columns and more particularly to fittings for holding the frit in place at the outlet of the column.

It is known to hold the packing in place in a liquid chromatographic column with a porous frit, which has sufficient stiffness and strength to hold the packing against substantial thrust pressure during operation of the chromatograph. The frit is held in place by a threaded fitting.

In a first prior art fitting of the known class, the frit is held by a threaded sleeve having a tapered swage or conical surface against which the column is sealed by threaded pressure on a conical ferrule. The frit has a diameter substantially equal to the outer diameter of the column.

In a second prior art fitting of the known class, the frit is held in a plastic ring, such as Kel-F ring, so the frit matches the inner diameter of the column.

The first prior art fitting has several disadvantages, such as: (1) the liquid extends through the frit beyond the inside diameter of the column and this causes some tailing; and (2) the seal is at the tapered joint and thus liquid may flow to that point, causing further tailing. The second type of fitting also has a disadvantage in that, if the plastic ring is compressed with use, or if the plastic ring or frit are too large or too small causing the seal around the column to open, liquid fills the cracks and voids to create tailing.

SUMMARY OF THE INVENTION

Accordingly, it is an object of the invention to provide a novel liquid chromatograph.

It is a further object of the invention to provide a novel chromatograph with reduced tailing caused by the method of mounting of the fittings to the chromatograph.

It is a still further object of the invention to provide a novel frit fixture for holding the frit at the end of the column of a chromatograph.

It is a still further object of the invention to provide a novel apparatus for mounting a chromatograph column.

It is a still further object of the invention to provide a novel method of making a frit.

It is a still further object of the invention to provide a novel frit that provides uniform flow-path lengths of a cross section of fluids between the chromatographic column and the flow cell.

In accordance with the above and further objects of the invention, a chromatographic column having an inner diameter of less than two millimeters has a fastening means on its bottom which cooperates with a frit sleeve. The frit sleeve has a complementary fastening means that permits it to be fastened to the column and hold a frit not substantially larger than the inner diameter of the column and has an opening in its bottom for accommodating the eluent from the column for passage directly through the frit into a flow cell.

A washer is positioned around the end of the column underneath its cylindrical wall to provide a liquid seal between the frit sleeve and the outlet end of the column. The frit may be press-fit in a cylindrical opening at the bottom of the sleeve aligned with the inlet to the flow cell or fastened within a metal ring or be bonded in place and may be tapered from the outlet of the column to the size of the inlet of the flow cell.

Because the inlet to the flow cell is smaller in diameter than the inner diameter of the chromatographic column, in some embodiments, the frit is shaped at one end to conform to the inner diameter of the column and at the other end to conform in shape to the inner diameter of the opening into the flow cell. Thus, one end of the frit will have a diameter or corresponding larger dimension if it is not circular, of no more than two millimeters and no less than ¼ of a millimeter, and the outlet is no greater than one millimeter and no less than 5/100ths of a millimeter.

In one embodiment, the frit is shaped as an inverted frustum of a right circular cone, with its base having a diameter substantially equal to the inner diameter of the chromatographic column and the circular cross-section of its truncated top having a diameter substantially equal to the inner diameter of the opening to the flow cell.

In one embodiment, the frit is formed of small particles of an alloy or of a first material. The particles have at least part of their surfaces coated with a second material or formed of an alloy. The small particles are sintered together at a temperature lower than the eutectic temperature but higher than their phase-immisibility temperature of the two materials to bind at locations of relatively small areas.

In the preferred embodiment, the particles are gold-plated nickel spheres sintered together in a gold-plated opening at a temperature lower than the gold-nickel eutectic temperature but higher than their phase-immisibility temperature. They are gold-plated carbonyl nickel powder, 29 percent by weight gold, electroless plated on INCO #255 nickel powder to form 2.5 micrometer diameter spherial particles. The pore size of the resulting frit is 250 nanometers after heat treating at 775 degrees Celsius for 60 minutes a 25% hydrogen, 75% argon atmosphere.

The size and shape of the frit is selected to reduce tailing by causing flow paths from the column to be uniform, both by shaping the size of the part that mates with the column and the part which mates with the inlet port of the flow cell, and also by using obstructions to certain centrally located flow paths to increase their flow length.

From the above description, it can be understood that the fittings of this invention have the advantages of: (1) having less dead space for the accumulation of fluid at the outlet of the chromatographic column; (2) providing a positive seal between the column and the frit sleeve; and (3) permitting the column to operate with less tailing.

SUMMARY OF THE DRAWINGS

The above noted and other features of the invention will be better understood from the following detailed description when considered in connection with the accompanying drawings, in which.

DETAILED DESCRIPTION

Figure 1:
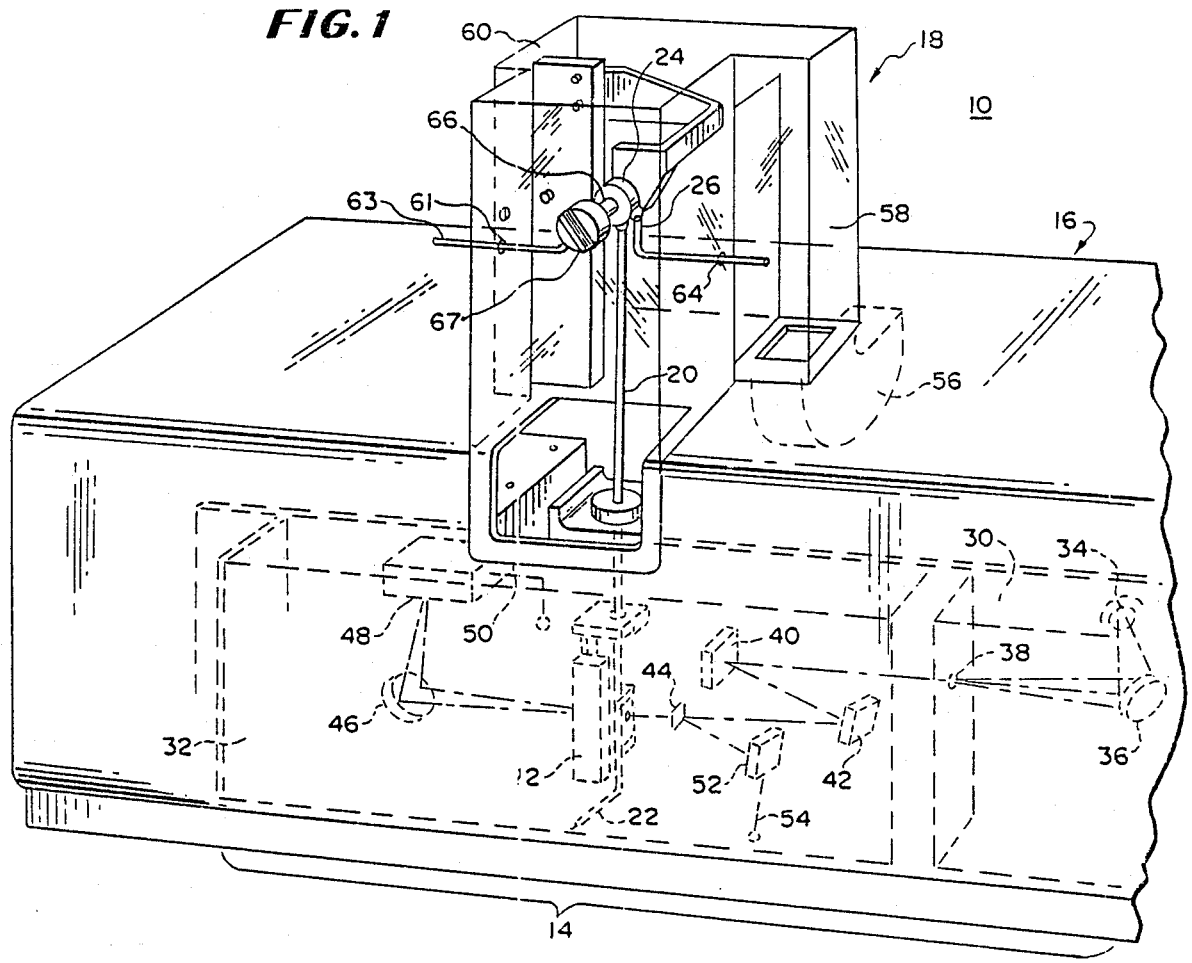
FIG. 1 is a fragmentary, simplified perspective view in accordance with an embodiment of the invention.

In FIG. 1, there is shown a simplified perspective view of a liquid chromatograph 10 having a flow cell assembly 12, a light path assembly 14, an electro-optical section 16 and an air flow control section 18. The light path assembly 14 generates and transmits light through the flow cell assembly 12 within the electro-optical section 16 while the air flow control section 18 controls the flow of air outside of the electro-optical section.

This apparatus 10 is a micro-liquid chromatograph. Micro-liquid chromatography is a form of high performance liquid chromatography that differs from conventional high performance liquid chromatography in that the inside diameter of the column is substantially less than the usual four to five millimeters, the flow rates are less than the usual one to five milliliters per minute, effluent detector volume is less than the usual four to 20 microliters and sample sizes are less than the usual 20 microliters. On the other hand, micro-scale chromatographs have internal column diameters of two millimeters or less, sample sizes less than five microliters and effluent detector volumes less than four microliters.

The flow cell assembly 12 is connected at its top end to a liquid chromatographic column 20 and at its bottom end to an eluate outlet 22. At the upper end of the column 20 is: (1) a sample injection valve 24 for applying samples to the chromatograph for analysis; and (2) a high pressure eluent inlet 26 from a source of eluent which is generally at ambient temperature.

The chromatograph itself may be cf any type but the perferred embodiment is directed to a micro-scale, high performance liquid chromatograph such as that described in patent application 300,567 filed by Robert W. Allington on Sept. 9, 1981, now U.S. Pat. No. 4, 422,942 and assigned to the same assignee as this application.

The light path assembly 14 includes a lamp assembly 30 and an optical compartment 32 mounted side-by-side so that light from the lamp assembly 30 is transmitted to the optical compartment 32 where it is caused to flow through the flow cell assembly 12 within the optical compartment 32. The lamp assembly itself is not part of this invention except insofar as it cooperates with the flow cell assembly 12. However, it includes a lamp 34 and an aspheric condensing mirror 36 which focuses light through a small slit at 38 into the optical compartment 32.

The optical compartment 32 includes an aspheric monochrometer focusing mirror 40, a diffraction grating assembly 42 and a beam splitter 44, which cooperates to transmit a portion of the light through the flow cell assembly 12 for reflection by a collecting mirror 46 onto a first detector 48 which generates a signal on conductor 50 and to focus a second portion of the light focused on a second detector 52 resulting in a signal on conductor 54. These signals are used to provide information about the sample as described in the below mentioned patent and as known in the art.

The electro-optical section 16 includes both the lamp assembly 30 and the optical compartment 32 as well as the electronic equipment necessary for a typical absorbance monitor resulting in output signals that provide information about the eluate flowing through the eluate outlet 22.

The absorbance monitor in the preferred embodiment is similar to the one disclosed in U.S. patent application Ser. No. 351,193 filed in the name of Robert W. Allington on Feb. 22, 1982, entitled ABSORBANCE MONITOR, and assigned to the same assignee as this application. However, the absorbance monitor has been modified to accommodate the chromatographic column and flow cell within the cabinet in the manner shown in FIG. 1 in the preferred embodiment. The specific absorbance monitor is not part of this invention.

The air flow control section 18 includes a blower 56, and air duct 58 and an air chamber 60. The air chamber 60 encloses the top of the liquid chromatographic column 20, the sample valve 24 and the eluent inlet 26. The walls of the air chamber 60 contain a first opening at 64 through which the eluent inlet 26 passes and a second opening 66 through which the sample valve 24 may be manipulated with knob 67.

Figure 2:
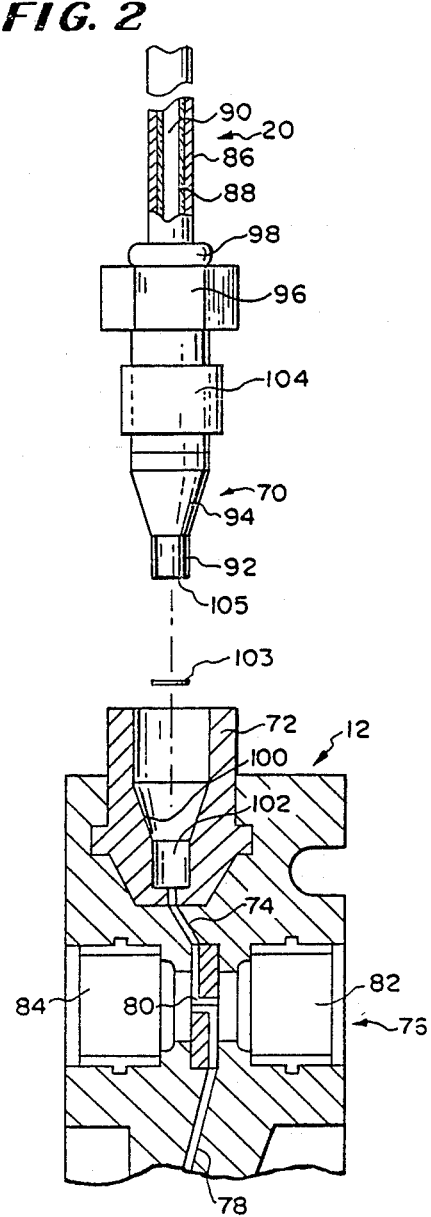
FIG. 2 is a fragmentary, exploded, partly broken-away elevational view of a portion of the embodiment of the invention of FIG. 1.

In FIG. 2, there is shown an exploded, fragmentary elevational view, partly broken away, of the flow cell assembly 12, the end fitting 70 and the liquid chromatographic column 20. In this figure, the flow cell assembly 12 and a portion of the liquid chromatographic column 20 are sectioned. The end fitting 70 mounts to the flow cell assembly 12 directly so that the liquid chromatographic column 20 is in close proximity to the inlet of the flow cell assembly 12. The end fitting 70 is mounted to the liquid chromatographic column 20 and holds the frit. While an end fitting is shown and described specifically for the bottom of the column, a similar frit may be mounted at the top of the column in a similar manner.

The flow cell assembly 12 includes an inlet connector 72, an inlet channel 74, an optical assembly 76 and an outlet channel 78. The inlet connector 72 receives the fluid from the liquid chromatographic column 20 and channels it into the inlet channel 74, from there to the optical assembly 76 and then through the outlet channel 78.

The optical assembly 76 includes a light channel 80 connected at one end to the inlet channel 74 and at the other end to the outlet channel 78 and aligned with window assemblies 82 and 84 so that light passing through the light channel 80 passes through the effluent and may be monitored. With this structure, the end of the liquid chromatographic column 20 is less than 30 millimeters from the light channel 80 and preferably less than 15 millimeters with an inlet channel 74 of less than 25 millimeters and preferably less than 15 millimeters to the light channel 80 to minimize the band broadening of the peaks.

The liquid chromatographic column 20 has steel cylindrical walls 86 and a very smooth surface on its bore adapted to contain within its center, packing material 90 in a manner known in the art. For columns of one millimeter and more inside diameter, it may be preferable that the smooth inside wall of the column be integral with the rest of the column, and made smooth by a finishing or polishing process such as liquid honing. Glass-lined interiors are likely to be preferable for smaller columns such as $\frac{1}{3}$ millimeter inside diameter. This is because of the difficulty of machinery thin, glass-lined sections. The liquid chromatographic column 20 is adapted to receive solvents for the elution of molecular species and must withstand high pressure in high performance liquid chromatographs.

The end fitting 70 includes a frit sleeve 92, a ferrule 94, a ferrule nut 96 and a retainer "O" ring 98. There is a similar end fitting 70 on the opposite end of the liquid chromatographic column 20 adapted to cooperate with a sample injector. The frit sleeve 92 is mounted at the end of the liquid chromatographic column 20 and has an outer end surface 105, spaced from the end of the chromatographic column by less than fifty thousandths of an inch. It contains a central aperture aligned with the central passageway of the liquid chromatographic column 20. The central aperture of the frit sleeve contains, in the preferred embodiment, the frit press-fitted therein.

In the preferred embodiment, the frit has a thickness of less than 40 thousandths of an inch and the end 105 of the frit sleeve 92 is only slightly more than that distance and less than 80 thousandths of an inch from the end of the liquid chromatographic column 20 to reduce the distance of fluid flow and thus reduce the broadening of the peak.

The ferrule 94 is adapted to fit within the inlet connector 72 and conforms in its outer cone to the ferrule opening at 100 which receives it in a tight engaging fit. The frit sleeve 92 extends into a conforming opening 102 in the inlet connector 72 and rests against a gasket 103 which has a central opening slightly larger than the inlet channel 74. The ferrule nut 96 can be threaded downwardly and move the sleeve portion 104 against the walls of the connector 72 to hold the ferrule 94 in place, thus pressing the gasket 103 between the end 105 of the frit sleeve and the bottom wall of the conforming opening 102 forming a liquid tight seal. The retainer "O" ring 98 prevents the ferrule nut 96 from rattling when it is loose.

With this configuration, the liquid chromatographic column 20 and end fitting 70 are inserted into the inlet connector 72 with the frit sleeve 92 fitting within a conforming opening 102 and having the central opening in the end surface 105 aligned with the inlet channel 74 for fluid to pass therethrough.

The ferrule 94 in one position loosely engages the walls of the ferrule opening 100 but is moved tightly against them by rotation of the ferrule nut 96. This forces the sleeve 104 into the ferrule 94, expanding it outwardly against the sides to tightly grip the inlet connector 72. The ferrule nut 96 and sleeve 104 are sold by Valco Instruments, P.O. Box 55603, Houston, Texas, under the part number ZN2. In this position, effluent flows through the liquid chromatographic column 20 directly from its outlet through a short thickness of frit into the inlet 74 and from there into the light channel 80 over a relatively short narrow path.

The flow cell 12 may be the type described in co-pending application for "Chromatographic Flow Cell and Method of Making It", U.S. patent application 585,347 filed by Robert W. Allington and John H. Jones on Mar. 1, 1984, now U.S. Pat. No. 4,575,424, the disclosure of which is incorporated herein by reference. The invention of this application provides special advantages when used with a flow cell according to the above-identified co-pending application to Allington et al because of the small inlet channel therein.

Figure 3:
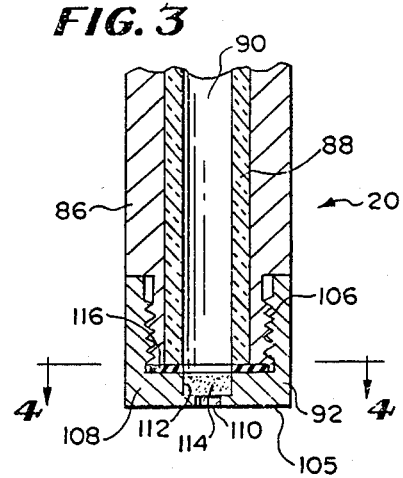
FIG. 3 is an enlarged, fragmentary, sectional view of a portion of the embodiment of FIG. 2.

In FIG. 3, there is shown an enlarged fragmentary sectional view of the frit sleeve 92 and the liquid chromatographic column 20 showing the packing material 90, the glass cylindrical inner lining 88 and the steel cylindrical column wall 86 recessed to form an annular shoulder with external threads at 106 around its lower cylindrical outer wall engaging inner threads along the inner portion of the cylindrical wall of the frit sleeve 92.

As shown in this view, the frit sleeve 92 has an inwardly extending end portion 108 forming an annular shoulder, a central recess 112 containing a frit at 114 and a central outlet 110 in the end 105. The annular inner shoulder supports a washer-shaped gasket 116 which engages the glass cylindrical inner lining 88 and a portion of the steel cylindrical wall 86 on its top and the annular shoulder on the bottom to form a liquid seal. The outer cylindrical wall of the frit sleeve 92 when threaded onto the end of the liquid chromatographic column 20 has its outer cylindrical surface flush with the surface of the column wall 86.

The central outlet 110 is centered in the recess 112 which receives the frit disk 114. The frit disk 114 may be of stainless steel particles sintered together to form a porous disk as known in the art or of other compositions described hereinafter. The frit disk 114 is press-fitted into the recess 112. The annular gasket 116 extends beyond the edge of the recess 112 a short distance and forms a seal between the end of the liquid chromatographic column 20 and the annular shoulder 108 to avoid the flow of liquid between the column wall and the frit sleeve 92 while permitting fluid to flow directly through the central outlet 110 into the inlet 74 (FIG. 2) of the flow cell assembly 12.

Figure 4:
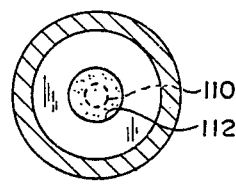
FIG. 4 is a sectional view through lines 4—4 of FIG. 3 of a portion of the embodiment of FIG. 3.

As best shown in FIG. 4, the central outlet 110 is approximately one-fourth the diameter of the frit disk 114 (FIG. 3) as indicated by the holding recess 112 and no greater than two-thirds the inside diameter of the column and, in the preferred embodiment, no greater than one millimeter. The frit holding recess 112 has a diameter equal to or slightly smaller than the inside diameter of the column and, in the preferred embodiment, should be no greater than 75 thousandths of an inch which corresponds to the size of the frit with the frit having a thickness of 20 thousandths of an inch in the preferred embodiment and no larger than 100 thousandths of an inch.

Instead of a counterbore through the bottom of a cup-like compartment to hold the frit as shown at 112, a stainless steel ring may fit within a cup about an opening in a thinner bottom and have mounted in its center a frit.

Figure 5:
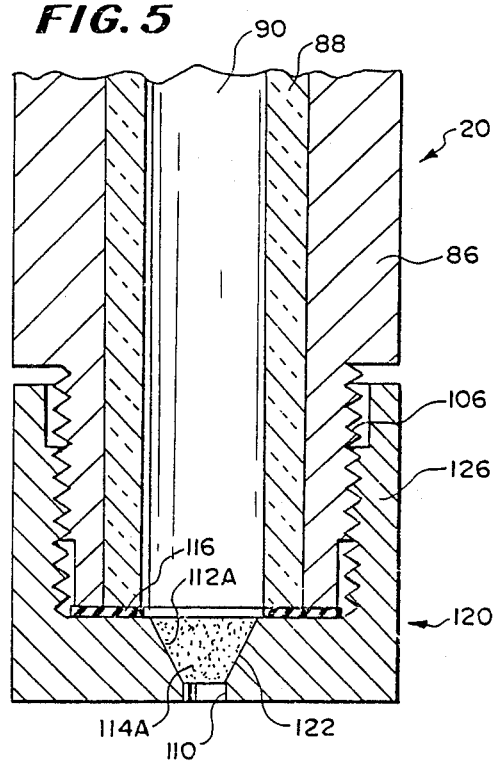
FIG. 5 is a fragmentary, sectional view of another embodiment of the portion of the embodiment of FIG. 2 shown in FIG. 3.

In FIG. 5, there is shown another embodiment of frit sleeve 120 engaging a liquid chromatographic column 20 and having a central outlet 110 similar to that of the embodiment of frit sleeve 92 shown in FIGS. 2-4. The liquid chromatographic column 20 is identical and similar parts are mounted in a similar manner except that the central outlet 110 is adapted to the packing material 90 in size by a frustum of a right circular cone or a truncated cone 122 instead of the cylindrically shaped frit recess 112. The frit 114A is formed within the funnel shaped recess 112A to hold the packing material 90.

The frit 114A is formed to grip the walls of the conical 122 solidly and extends from the central outlet 110 sized to the inlet channel 74 (FIG. 2) upwardly to the packing material 90 conforming on one end to the outlet 110 and at the other to the inside diameter of the column 20. The frit 114A is bonded to the walls of the recess 112A to hold the frit in place and to prevent packing from flowing or the gasket may have a smaller aperture and thus extend over and seal the recess. With this configuration, the conical flow pattern reduces band spreading within the frit.

Figure 7:
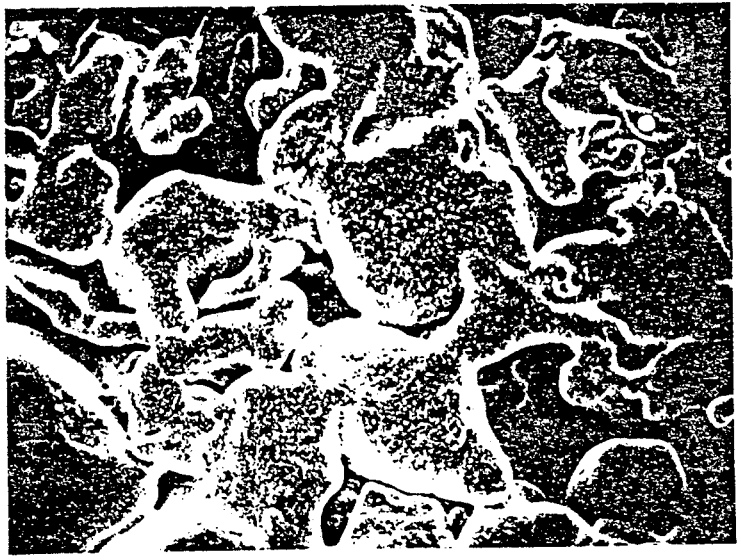
FIG. 7 is a schanning electron micrograph of a prior art frit magnified 800 times.
Figure 6:
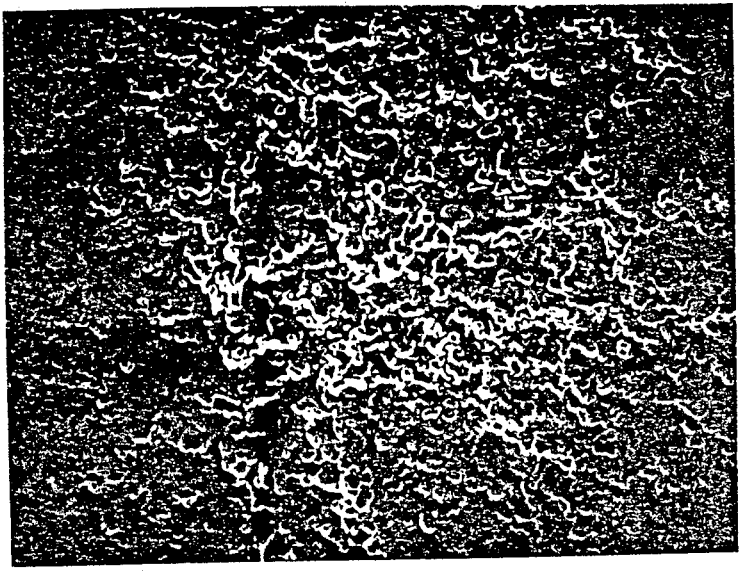
FIG. 6 is a scanning electron micrograph of a frit in accordance with the invention, magnified 800 times.

In FIG. 6 there is shown a photomicrograph magnified 800 times of the surface of particles which are bonded together to make the frit 114A in the preferred embodiment. On the other hand, FIG. 7 shows a photomicrograph of the particles found in the prior art frit also magnified 800 times. The prior art frit of FIG. 7 was cold pressed whereas the frit of FIG. 6 is formed by sintering the particles together in a properly shaped opening in the sleeve. Thus, the frit is bonded to the walls of the sleeve and may conform to a desired shape. With this type of frit, the porosity is more regular, the frit itself is stronger and it may be formed to a shape that permits more streamlined flow.

Figure 8:
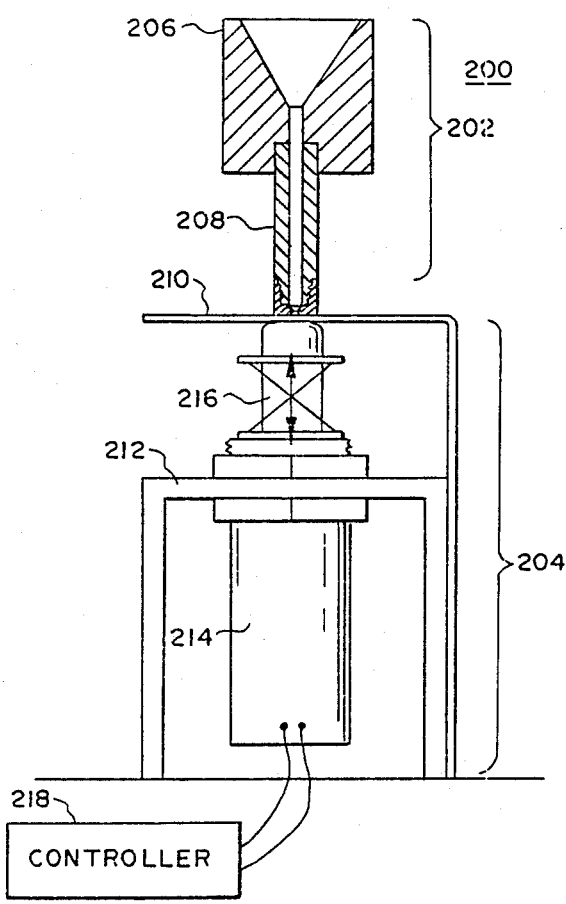
FIG. 8 is an enlarged view of a fixture used in accordance with an embodiment of the invention.

In FIG. 8, there is shown a fixture 200 adapted to form frit 114A (FIG. 5) within a frit sleeve 120 (FIG. 5). Prior to sintering the frit in the frit sleeve 120, the particles forming the frit are packed into the frit sleeve 120 using tools to be described hereinafter in connection with FIGS. 11 and 12. The fixture 200 includes as its principal parts a funnel assembly 202 and a vibrator section 204 mounted together to pack the frit particles into a sleeve 120.

To permit insertion into the frit sleeve 120, the funnel assembly 202 includes a funnel 206 and a frit sleeve adapter 208. The firt sleeve adapter is similar in size and structure to a chromatographic column 20 (FIG. 5) but without packing material and is adapted to engage a frit sleeve 120 in a similar manner to the column 20. While a frit sleeve 120 adapted to contain a connical frit 114A in a funnel-shaped recess 112A is shown, the shape of the frit and recess may vary and may, if desirable, be cylindrical such as the frit 114 or other the irregular shape.

To aid in packing the frit particles into the sleeve 120, the vibrator section 204 includes a movable sleeve plate 210, a frame 212, a solenoid 214, a plunger 216 and a control circuit 218.

The frame 212 supports the plunger 216, movable sleeve plate 210 and solenoid 214, with the plunger 216 positioned to be moved against the plate 210 by the solenoid 214 to vibrate the plate 210 and the sleeve 120. The solenoid 214 is electrically connected to a controller 218 which upon activation transmits electrical oscillation to the solenoid to cause the plunger to vibrate the plate 210.

Figure 9:
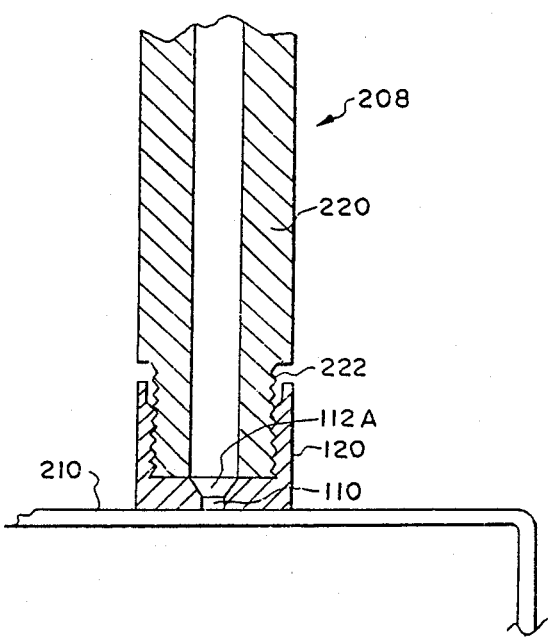
FIG. 9 is an enlarged fragmentary sectional view of a portion of the fixture of FIG. 8.

In FIG. 9, there is shown an enlarged fragmentary view of the adapter 208, frit sleeve 120 and vibrator plate 210. As best shown in this view, the adapter 208 includes a column 220 having dimensions substantially the same as the column 20 (FIG. 3) with external threads 222 at one end to engage the frit sleeve 120 in a manner similar to a column to permit frit particles to drop into the central column 110 and recess 112A.

Figure 10:
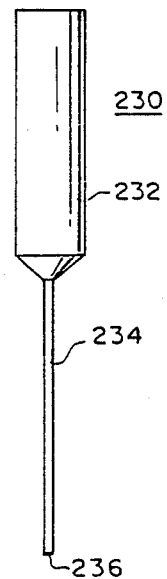
FIG. 10 is an elevational view of a packing tool used in an embodiment of the invention.

In FIG. 10, there is shown a frit packing tool 230 having a handle portion 232 and a wire portion 234. The wire portion 234 is: (1) cylindrical; (2) has a diameter of less than two millimeters and a length of between one inch and ten inches; (3) is connected at one end to the handle 232; and (4) has a flat surface 236 substantially perpendicular to the longitudinal axis of the wire at the other end.

Figure 11:
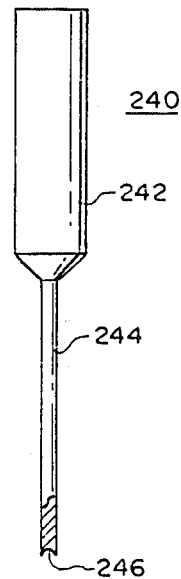
FIG. 11 is an elevational view of another packing tool used in an embodiment of the invention.

In FIG. 11, there is shown a second packing tool 240 having a handle 242 and a wire portion 244. The wire portion 244: (1) is cylindrical; (2) has a diameter of less than two millimeters and the same as the diameter of the cone base for the opening 112A; (3) has a length of between one inch and ten inches; (4) is connected at one end to the handle 242; and (5) has a concave surface 246 at its other end. The concave surface is used to pack frit in the cone opening 112A to permit shrinkage during sintering.

Prior to sintering the frit, it is formed of particles within the sleeve. To accomplish this, a very small amount of particles are put in the funnel 206 and dropped downwardly through the central hole in the adaptor 208 and into the cylindrical opening 110 below the conical opening 112A in frit sleeve 120.

In the packing operation, the operating packing tool 230 is used first to pack the particles into the cylindrical opening 110. The rod or wire 234 is fastened to tool 230 fits smoothly into the diameter of cylindrical opening 110 and stamps the particles into opening 110. This opening is not filled in FIG. 5 and its filling can be omitted with a slight loss of chromatographic performance.

Next, a weighed amount of additional particles are poured into funnel 206. Solenoid 216 is pulsed repeatedly, causing its plunger 216 to tap against plate 210 upon which frit sleeve 120 rests. This vibrating action packs the particles down into cone 22.

After the particles are packed, second operation packing tool 240 with concave ended rod 244 is pushed down the central hole of the frit sleeve adaptor 208 to finish packing the particles in the conical opening 112A of the frit sleeve 120. The diameter of rod 244 is the same as the diameter of the base (upper end) of cone 112A. The concave end of the rod 244 leaves a mounded top on the packed particles. The mounded top of the packed particles is desirable because the particles settle slightly during sintering.

Figure 12:
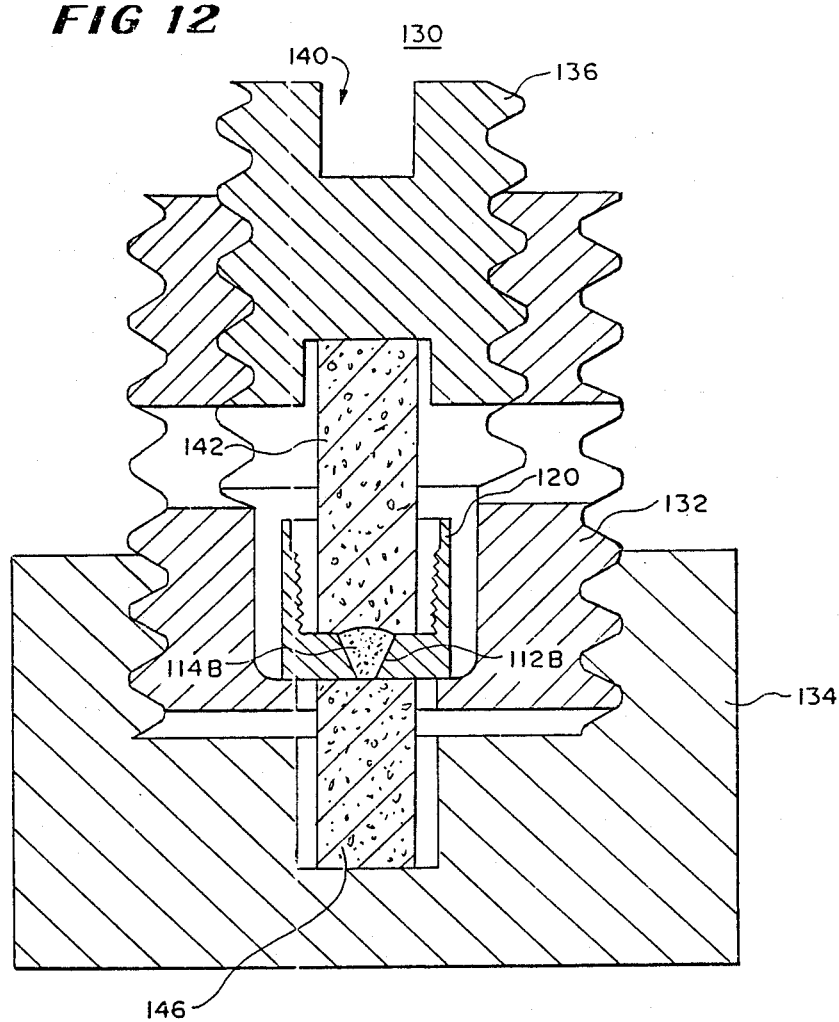
FIG. 12 is a sectional view of a fixture used in accordance with the embodiment of FIG. 5.

In FIG. 12, there is shown a fixture 130 in which there is mounted a sleeve 120 similar to the sleeve 120 (FIG. 5) but adapted to the new frit and method of making the new frit shown at 114B within the opening 122A bounded by the walls 112B.

The fixture 130 includes a first die part 132, a base 134 and a second die part 136, which cooperate together to permit sintering of the particles to form the frit 114B within the sleeve 120. The base 134 is adapted to mount a graphite column 140 which may be made of a material typical of electro-graphitic motor brushes and to receive threaded within it the die 132 to hold the sleeve 120 in place with the particles to be sintered located at 114B.

Within sleeve 120, the aperature 112B shaped in accordance with the frit, is gold-plated. A second carbon column 142 is mounted within the sleeve and contacts a recess in the second die fixture 132 which is threaded in the top of the die fixture 132 and has a screw slot 140 in its upper end so that it may be threaded downwardly to exert mild pressure on the frit 114B between the columns 140 and 142.

The particles forming the frit are gold-plated nickel spheres. More specifically, they are gold-plated carbonyl nickel powder, 29 percent by weight gold, electroless plated on INCO #255 nickel powder to form 2.5 micrometer diameter spherical particles. The fixture 130 with the frit in place and pressure exerted by tightening with the screw 140 is heated in a standard controlled-atmosphere heat-treating furnace at 775 degrees Celsius for 60 minutes in a 25% hydrogen, 75% argon atmosphere.

The frit that is formed in this manner conforms to and is bonded to the opening 112B which is of a size and shape selected to reduce tailing by causing flow paths from the column to be as uniform as possible, both by shaping the size of the part that mates with the column and the part which mates with the inlet port of the flow cell, and also by using obstructions to certain centrally located flow paths to increase their flow length.

In one embodiment, the frit is shaped as an inverted frustum of a right circular cone, with its base having a diameter equal to the inner diameter of the chromatographic column and the circular cross-section of its truncated top having a diameter equal to the inner diameter of the opening to the flow cell.

In the preferred embodiment, the frit is formed of small particles of an alloy or of a first material having at least part of their surfaces coated with a second material, which may a pure material or an alloy. The particles are sintered together and preferably are sintered inside the actual frit sleeve 126A, which is made of stainless steel coated with the second material as described. The coating on the aperature 112B is of the same material in the preferred embodiment as the coating on the particles to be sintered together.

The temperature is selected to be lower than the eutectic temperature of an alloy formed by the coating and the base of the particles to bind at locations of relatively small areas. In the case of a nickel particle plated with gold, the temperature is lower than the gold-nickel eutectic temperature but higher than their phase-immisibility temperature. More generally, the particles are placed in an opening in a sleeve to form a shape having a larger top than a bottom and heated to a temperature sufficiently high to cause them to bind to each other and to the walls of said opening in said sleeve. The particles contain at least two materials having an eutectic temperature and the fixture is heated to a temperature high enough to cause rapid diffusion but below the said eutectic temperature.

Although a preferred embodiment of the invention has been described with some particularity, many modifications and variations in the preferred embodiment are possible without deviating from the invention. Therefore, it is to be understood that, within the scope of the appended claims, the invention may be practiced other than as specifically described.

What is claimed is:

1. An apparatus comprising:
   a chromatographic column having an inner diameter of no more than two millimeters;
   said chromatographic column having a cylindrical externally threaded recessed portion in its outer wall at least at one end;
   cylindrical tubular sleeve means having internal threads adapted to cooperate with the external threads on said column;
   said sleeve means having an annular shoulder in its interior and an end portion;
   the one end of said chromatographic column being less than 150 thousandths of an inch from the end portion of the sleeve;
   said annular shoulder being adapted to form a cylindrical opening less than 79 thousandths of an inch in diameter;
   said cylindrical opening having a frit therein, whereby packing may be held against substantial thrust forces in the column;
   the thickness of said frit being less than one hundred thousandths of an inch;
   a flow cell;
   an inlet connector for said flow cell;
   fastening means for fastening said sleeve to the inlet connector of the flow cell whereby fluid flows from the column into the flow cell;
   a flow cell inlet channel;
   said inlet channel having a diameter less than one millimeter;
   the frit being spaced from the inlet channel by the end portion of the sleeve, said end portion including an opening aligned with the inlet channel, whereby fluid flows through the opening in the end portion into the inlet channel;
   a light channel in said flow cell;
   said inlet channel communicating with the light channel in the flow cell;
   the fluid path between the end of said frit and said light channel being less than 25 millimeters; and
   said light channel being at right angles to the central axis of said column.

2. An apparatus comprising:
   a chromatographic column having an inlet and an outlet;
   said chromatographic column having a portion in its wall at least at one end with first fastening means thereon;
   sleeve means having second fastening means adapted to cooperate with the first fastening means;
   an opening in said one end;
   an aligned opening in said sleeve means aligned with the opening in said one end and adjacent thereto;
   said aligned opening having a stiff porous member of sintered particles therein, whereby packing may be held against substantial thrust forces in the column;
   the inner diameter of said column being no more than two millimeters;
   the porous member including a top surface and a bottom surface of different sizes;
   the top surface being of same area and shape as the outlet of the chromatographic column;
   a flow cell having a light path and inlet for communicating with said opening;
   the distance between said opening and said flow cell being less than 25 millimeters;
   a shoulder adjacent to said opening;
   sealing means for sealing said shoulder to the wall of said chromatographic column;

said shoulder being an annular shoulder around said opening and aligned with said wall of said column; and the bottom surface of said porous member being smaller than the top surface and substantially the same size as said inlet.

3. An apparatus according to claim 2 further comprising:

a shoulder adjacent to said opening;

sealing means for sealing said shoulder to the wall of said chromatographic column;

said shoulder being an annular shoulder around said opening and aligned with said wall of said column.

4. An apparatus according to claim 3 in which said porous member is a frit formed of coated particles.

5. An apparatus according to claim 4 in which the stiff porous member is a frit having a diameter less than 79 thousandths of an inch.

6. An apparatus according to claim 5 in which the frit is less than 100 thousandths of an inch thick.

7. An apparatus according to claim 6 in which the particles are gold-plated nickel and the opening is gold plated.

8. An apparatus according to claim 4 in which the particles are gold-plated nickel and the opening is gold-plated.

9. An apparatus according to claim 2 in which said porous member is a frit formed of coated particles.

10. An apparatus according to claim 9 in which the stiff porous member is a frit having a diameter less than 79 thousandths of an inch.

11. An apparatus according to claim 10 in which the frit is less than 100 thousandths of an inch thick.

12. An apparatus according to claim 11 in which the particles are gold-plated nickel and the opening is gold plated.

13. An apparatus according to claim 2 in which the stiff porous member is a frit having a diameter less than 79 thousandths of an inch.

14. An apparatus according to claim 13 in which the frit is less than 100 thousandths of an inch thick.

15. An apparatus according to claim 2 in which:

said chromatographic column has an inlet means;

said inlet means includes means for supporting a frit;

an inlet frit in said means for supporting a frit;

said inlet frit having a top surface and a bottom surface of different sizes;

said top surface of said inlet frit being larger than said bottom surface of said inlet frit.

* * * * *